United States Patent [19]

Pellacini et al.

[11] Patent Number: 5,847,092
[45] Date of Patent: Dec. 8, 1998

[54] ERYTHROMYCIN A 9-0 OXIME DERIVATIVES ENDOWED WITH ANTIBIOTIC ACTIVITY

[75] Inventors: Franco Pellacini; Giovanna Schioppacassi, both of Milan; Enrico Albini, Pavia; Daniela Botta, Como; Stefano Romagnano; Francesco Santangelo, both of Milan, all of Italy

[73] Assignee: Zambon Group S.p.A., Vicenza, Italy

[21] Appl. No.: 836,785

[22] PCT Filed: Dec. 7, 1995

[86] PCT No.: PCT/EP95/04815

§ 371 Date: May 16, 1997

§ 102(e) Date: May 16, 1997

[87] PCT Pub. No.: WO96/18633

PCT Pub. Date: Jun. 20, 1996

[30] Foreign Application Priority Data

Dec. 13, 1994 [IT] Italy .................................. MI94A2496

[51] Int. Cl.$^6$ ............................. C12P 19/62; A01K 31/70
[52] U.S. Cl. ................................................ 536/7.2; 514/29
[58] Field of Search .................................. 536/7.2; 514/29

[56] References Cited

U.S. PATENT DOCUMENTS

| | | | |
|---|---|---|---|
| 4,349,545 | 9/1982 | d'Ambrieres et al. | 514/49 |
| 4,740,502 | 4/1988 | Hannick et al. | 514/29 |
| 5,302,705 | 4/1994 | Misawa et al. | 536/7.4 |
| 5,444,051 | 8/1995 | Agouridas et al. | 514/29 |

OTHER PUBLICATIONS

Journal of Antibiotics, vol. 44, No. 3, Mar. 1991, Tokyo, JP, pp. 313–330, XP000567789, J. Gasc et al: "New ether oxime derivatives of erythromycin A. A structure–activity relationship study".

*Primary Examiner*—Gary L. Kunz
*Attorney, Agent, or Firm*—Nikaido Marmelstein Murray & Oram, LLP

[57] ABSTRACT

Erythromycin 9-oxime derivatives wherein a phenyl or heterocylic group is attached indirectly to the 9-position of erythromycin A through an alkylene diamine bridging member. These compounds exhibit broad spectrum antibiotic activity.

7 Claims, No Drawings

ERYTHROMYCIN A 9-0 OXIME DERIVATIVES ENDOWED WITH ANTIBIOTIC ACTIVITY

The present invention relates to Erythromycin A derivatives endowed with antibiotic activity, useful in the treatment of infectious diseases and, more particularly, it relates to Erythromycin A 9-[0-(aminoalkyl)oxime] derivatives endowed with antibiotic activity against Gram-positive and Gram-negative microorganisms. Erythromycin A [The Merck Index, XI Ed., No. 3626] is a well-known naturally occurring macrolide endowed with antibiotic activity, having the following structure

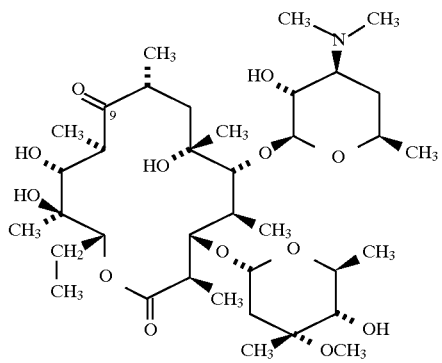

Besides being active against some non-bacterial microorganisms such as rickettsiae and mycoplasmas, Erythromycin A is endowed with antibacterial activity mainly against Gram-positive microorganisms such as streptococci, staphylococci and pneumococci, but it results effective as well against some Gram-negative microorganisms such as, for instance, Haemophilus influenzae, *Neisseria gonorrhoeae* and *Bordetella pertussis*.

In addition to the well-known activity against the aforementioned prokaryotes, it has been recently described in the literature that Erythromycin A and other macrolide antibiotics are active against eukaryotic parasites [P. A. Lartey et al., Advances in Pharmacology, 28, 307–343 (1994)].

Also in the case of Erythromycin A, likewise other antibacterial drugs, phenomena of resistance were observed with some bacterial strains.

In particular, the phenomenon was observed in the treatment of infections caused by staphylococci following to prolonged administration of Erythromycin A [A. Kucers and N. McK. Bennett, The use of antibiotics, A Comprehensive Review with Clinical Emphasis, William Heinemann Medical, IV Ed., (1987) 851–882].

The interest towards macrolide antibiotics derives from their use in clinical and veterinary therapy in the treatment of several infectious diseases such as, for instance, the infections of the respiratory tract, of the gastrointestinal tract, of the urogenital tract and of the external organs like skin, eye and ear.

Because of its high instability in acidic environment Erythromycin A is irreversibly converted, for instance in the gastrointestinal tract following to oral administration, into derivatives devoid of antibiotic activity, conferring thus poor bioavailability on the active principle [H. A. Kirst, Annual Reports in Medicinal Chemistry, 25, 119–128 (1989)].

In order to overcome the above drawbacks, the research was addressed to compounds which, while maintaining the good antibiotic properties of Erythromycin A, resulted to be characterized by a superior stability to the acids and better pharmacokinetic properties such as, for instance, superior oral bioavailability, haematic concentration, tissue penetration and half-life.

Within this field, we can cite as an example the carbamates and carbonates of Erythromycin A or Erythromycin A 9-0-oxime described in the European patent applications No. 0216169 and No. 0284203 (both in the name of Beecham Group PLC) and the compounds described in the European patent application No. 0033255 (Roussel-Uclaf). The European patent application No. 0033255, in particular, describes derivatives of Erythromycin A 9-0-oxime of formula

wherein

Ery represents the Erythromycin A residue wherein the oxime group (—N=Ery) is in place of the carbonyl group in position 9 (0=Ery); A represents a straight or branched alkyl group with from 1 to 6 carbon atoms; R represents, inter alia, an optionally substituted alkoxy group with from 1 to 6 carbon atoms, or a group [—N($R_1$)$R_2$] wherein $R_1$ and $R_2$, the same or different, represent a hydrogen atom or an optionally substituted alkyl group with from 1 to 6 carbon atoms.

The compounds described in the European patent application No. 0033255 such as, for instance, Erythromycin A 9-[0-[(2-methoxyethoxy)methyl]oxime], known with the International Nonproprietary Name Roxithromycin [The Merck Index, XI Ed., No. 8253], Erythromycin A 9-[0-[(2-dimethylamino)ethyl]oxime] and Erythromycin A 9-[0-[(2-diethylamino)ethyl]oxime] have a spectrum of activity in vitro comparable to that of Erythromycin A but are endowed with a superior stability to the acids and better pharmacokinetic properties.

Said compounds, therefore, present an antibiotic activity against Gram-positive bacteria such as staphylococci, streptococci and pneumococci and against some Gram-negative bacteria such as, for instance, *Haemophilus influenzae* and *Haemophilus pertussis*.

Now we have found compounds derivative of Erythromycin A 9-0-oxime and, more particularly, compounds derivative of Erythromycin A 9-[0-(aminoalkyl)oxime], partly comprised but not exemplified in the European patent application No. 0033255, which have a wider spectrum of antibacterial activity against Gram-positive microorganisms and, particularly, against Gram-negative microorganisms, and improved pharmacokinetic properties such as, for instance, a superior duration of action and a superior half-life of tissue elimination, with respect to the compounds described in the aforementioned European patent application.

Object of the present invention, therefore, are the compounds of formula

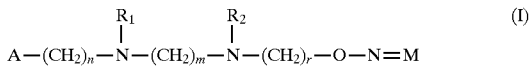

wherein

A is a phenyl group or a heterocycle with 5 or 6 members containing 1 or more heteroatoms selected among nitrogen, oxygen and sulphur, optionally substituted with from 1 to 3 groups, the same or different, selected among straight or branched $C_1$–$C_4$ alkyl or alkoxy groups, $C_1$–$C_2$ alkylenedioxy groups, $C_1$–$C_4$ alkylsulphonyl groups, phenyl, phenoxy, hydroxy, carboxy, nitro, halogen and trifluoromethyl groups;

$R_1$ and $R_2$, the same or different, represent a hydrogen atom or a straight or branched $C_1$–$C_4$ alkyl groups;

n is 1 or 2;
m is an integer comprised between 1 and 8;
r is an integer comprised between 2 and 6;
M represents a group of formula

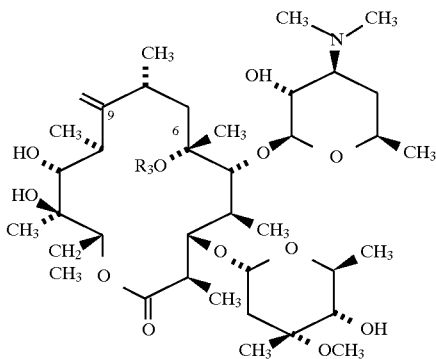

wherein
$R_3$ is a hydrogen atom or a methyl group;
and pharmaceutically acceptable salts thereof.

The oximes of formula (I) can have Z or E configuration.

Object of the present invention, therefore, are the compounds of formula (I) having Z or E configuration, with a preference for these latter.

The compounds of formula (I) are endowed with antibiotic activity and are characterized by a high stability to the acids and by good pharmacokinetic properties, being thus used in human or veterinary therapy for the treatment of several infectious diseases such as, for instance, the infections of the central nervous system, of the upper and lower respiratory tract, of the gastrointestinal tract, of the urogenital tract, of the odontological tissue and of the external organs such as skin, eye and ear.

In the present description, unless otherwise specified, with the term $C_1$–$C_4$ alkyl group we intend a straight or branched $C_1$–$C_4$ alkyl such as methyl, ethyl, n.propyl, isopropyl, n.butyl, isobutyl, sec-butyl and tert-butyl group; with the term $C_1$–$C_4$ alkoxy group we intend a straight or branched $C_1$–$C_4$ alkoxy such as methoxy, ethoxy, n.propoxy, isopropoxy, n.butoxy, isobutoxy, sec-butoxy and tert-butoxy group; with the term $C_1$–$C_2$ alkylenedioxy group we intend a methylenedioxy or ethylenedioxy group.

With the term heterocycle with 5 or 6 members containing 1 or more heteroatoms selected among nitrogen, oxygen and sulphur we intend a heterocycle preferably selected among pyridine, pyrrole, pyrrolidine, furan, tetrahydrofuran and thiophene.

Preferred compounds are the compounds of formula (I) wherein A represents a phenyl group or a heterocycle selected between pyridine and furan, optionally substituted with from 1 to 3 groups selected among hydroxy, methoxy, methylenedioxy, n.butoxy, phenoxy, phenyl, methylsulphonyl, nitro, halogen and trifluoromethyl groups; $R_1$ and $R_2$, being the same, represent a hydrogen atom or a methyl group; $R_3$ represents a hydrogen atom.

Still more preferred compounds are the compounds of formula (I) wherein A represents a phenyl group optionally substituted with a group selected among phenoxy, nitro and trifluoromethyl; $R_1$ and $R_2$, being the same, represent a hydrogen atom or a methyl group; n is equal to 1; m is equal to 6; r is equal to 2; $R_3$ represents a hydrogen atom.

Pharmaceutically acceptable salts of the compounds of formula (I) are the salts with organic or inorganic acids such as, for instance, hydrochloric, hydrobromic, hydroiodic, nitric, sulphuric, phosphoric, acetic, tartaric, citric, benzoic, succinic and glutaric acid. Specific examples of preferred compounds of formula (I) are:

Erythromycin A (E)-9-[0-[2-[6-(phenylmethylamino) hexylamino]ethyl]oxime];
Erythromycin A (E)-9-[0-[2-[2-(phenylmethylamino) ethylamino]ethyl]oxime];
Erythromycin A (E)-9-[0-[6-[6-(phenylmethylamino) hexylamino]hexyl]oxime];
Erythromycin A (E)-9-[0-[6-[3-(phenylmethylamino) propylamino]hexyl]oxime];
Erythromycin A (E)-9-[0-[6-[5-(phenylmethylamino) pentylamino]hexyl]oxime];
Erythromycin A (E)-9-[0-[2-[8-(phenylmethylamino) octylamino]ethyl]oxime];
Erythromycin A (E)-9-[0-[2-[5-(phenylmethylamino) pentylamino]ethyl]oxime];
Erythromycin A (E)-9-[0-[5-[6-(phenylmethylamino) hexylamino]pentyl]oxime];
Erythromycin A (E)-9-[0-[3-[6-(phenylmethylamino) hexylamino]propyl]oxime];
Erythromycin A (E)-9-[0-[3-[4-(phenylmethylamino) butylamino]propyl]oxime];
Erythromycin A (E)-9-[0-[2-[N-methyl-6-(N'-methyl-N'-phenylmethylamino)hexylamino]ethyl]oxime];
Erythromycin A (E)-9-[0-[2-[6-[(biphenyl-4-yl) methylamino]hexylamino]ethyl]oxime];
Erythromycin A (E)-9-[0-[2-[6-[(3-phenoxyphenyl) methylamino]hexylamino]ethyl]oxime];
Erythromycin A (E)-9-[0-[2-[6-[(4-phenoxyphenyl) methylamino]hexylamino]ethyl]oxime];
Erythromycin A (E)-9-[0-[2-[6-(2-furylmethylamino) hexylamino]ethyl]oxime];
Erythromycin A (E)-9-[0-[2-[6-(3-pyridylmethylamino) hexylamino]ethyl]oxime];
Erythromycin A (E)-9-[0-[2-[6-[(4-methoxyphenyl) methylamino]hexylamino]ethyl]oxime];
Erythromycin A (E)-9-[0-[2-[6-[(4-n.butoxyphenyl) methylamino]hexylamino]ethyl]oxime];
Erythromycin A (E)-9-[0-[2-[6-[(3,4-methylenedioxyphenyl)methylamino]hexylamino]ethyl] oxime];
Erythromycin A (E)-9-[0-[2-[6-[(4-methylsulphonylphenyl) methylamino]hexylamino]ethyl]oxime];
Erythromycin A (E)-9-[0-[2-[6-[(4-fluorophenyl) methylamino]hexylamino]ethyl]oxime];
Erythromycin A (E)-9-[0-[2-[6-[(2-trifluoromethylphenyl) methylamino]hexylamino]ethyl]oxime];
Erythromycin A (E)-9-[0-[2-[6-[(3-trifluoromethylpheriyl) methylamino]hexylamino]ethyl]oxime];
Erythromycin A (E)-9-[0-[2-[6-[(4-trifluoromethylphenyl) methylamino]hexylamino]ethyl]oxime];
Erythromycin A (E)-9-[0-[2-[6-[(2-hydroxyphenyl) methylamino]hexylamino]ethyl]oxime];
Erythromycin A (E)-9-[0-[2-[6-[(3-hydroxyphenyl) methylamino]hexylamino]ethyl]oxime];
Erythromycin A (E)-9-[0-[2-[6-[(4-hydroxyphenyl) methylamino]hexylamino]ethyl]oxime];
Erythromycin A (E)-9-[0-[2-[6-[(3,5-dichloro-2-hydroxyphenyl)methylamino]hexylamino]ethyl]oxime];
Erythromycin A (E)-9-[0-[2-[6-[(2-nitrophenyl) methylamino]hexylamino]ethyl]oxime];
Erythromycin A (E)-9-[0-[2-[6-[(3-nitrophenyl) methylamino]hexylamino]ethyl]oxime];
Erythromycin A (E)-9-[0-[2-[6-[(4-nitrophenyl) methylamino]hexylamino]ethyl]oxime];
Erythromycin A (E)-9-[0-[2-[6-[(4-hydroxy-3-nitrophenyl) methylamino]hexylamino]ethyl]oxime];

Erythromycin A (E)-9-[0-[2-[6-[(3-hydroxy-4-nitrophenyl) methylamino]hexylamino]ethyl]oxime];

Erythromycin A (E)-9-[0-[2-[N-methyl-6-[N'-methyl-N'-(4-trifluoromethylphenyl)methylamino]hexylamino]ethyl] oxime].

The preparation of the compounds of formula (I), object of the present invention, can be carried out according to the synthetic method which is described below.

The method comprises, at first, the condensation reaction between a suitable amino acid of formula $$HN(R_1)-(CH_2)_{m-1}-COOH \quad (II)$$

wherein $R_1$ and m have the above reported meanings;
with an acyl chloride of formula $$A-(CH_2)_{n-1}-COCl \quad (III)$$

wherein

A and n have the above reported meanings.

The condensation reaction is carried out, according to conventional techniques, in an inert solvent and in the presence of a base such as, for instance, an alkali metal hydroxide, to obtain the compounds of formula $$A-(CH_2)_{n-1}-CON(R_1)-(CH_2)_{m-1}-COOH \quad (IV)$$

wherein

A, $R_1$, n and m have the above reported meanings.

The thus obtained N-acyl amino acids of formula (IV) are further condensed, according to conventional techniques, with an amino ester of formula $$HN(R_2)-(CH_2)_{r-1}-COOR_4 \quad (V)$$

wherein $R_2$ and r have the above reported meanings;
$R_4$ represents a methyl or ethyl group;
to obtain the compounds of formula $$A-(CH_2)_{n-1}-CON(R_1)-(CH_2)_{m-1}-CON(R_2)-(CH_2)_{r-1}-COOR_4 \quad (VI)$$

wherein

A, $R_1$, $R_2$, $R_4$, n, m and r have the above reported meanings.

By working according to conventional techniques the compounds of formula (VI) are subsequently reduced, for instance with sodium boron hydride in the presence of acids, lithium aluminum hydride, dimethyl sulphide-borane or by catalytic hydrogenation, to the corresponding amino alcohols of formula $$A-(CH_2)_n-CON(R_1)-(CH_2)_m-CON(R_2)-(CH_2)_r-OH \quad (VII)$$

wherein

A, $R_1$, $R_2$, n, m and r have the above reported meanings.

The amino alcohols of formula (VII) are then converted into the corresponding sulphonyl derivatives of formula (VIII), for instance by means of methanesulphonyl chloride or p.toluenesulphonyl chloride, and subsequently condensed with Erythromycin A 9-0-oxime or 6-0-methylerythromycin A 9-0-oxime, both representable according to formula (IX), to obtain the compounds of formula (I)

$$(VII) \longrightarrow A-(CH_2)_n-N(R_1)-(CH_2)_m-N(R_2)-(CH_2)_r-OR_5 \quad (VIII)$$

$$\downarrow M=N-OH \quad (IX)$$

$$A-(CH_2)_n-N(R_1)-(CH_2)_m-N(R_2)-(CH_2)_r-O-N=M \quad (I)$$

wherein

A, $R_1$, $R_2$, M, n, m and r have the above reported meanings;

$R_5$ represents a mesyl or tosyl group.

The reaction between the compounds of formula (VIII) and the oximes of formula (IX) is carried out in an inert organic solvent such as, for instance, tetrahydrofuran, ethyl ether or 1,2-dimethoxyethane, in the presence of potassium tert-butylate and of 18-crown-6 ether as complexing agent.

It is clear to the man skilled in the art that when the sulphonylation reaction is carried out by using the compounds of formula (VII) wherein one or both $R_1$ and $R_2$ substituents represent a hydrogen atom, it can be necessary to protect the nitrogen atom or atoms, before carrying out the sulphonylation reaction.

In that case, the condensation of the thus obtained N-protected sulphonyl derivatives with the oximes of formula (IX), analogously to what previously reported, and the subsequent deprotection carried out according to conventional methods, allow to obtain the compounds of formula (I) wherein one or both $R_1$ and $R_2$ substituents represent a hydrogen atom.

For a bibliographic reference to the protection of amines see [T. W. Greene and P. G. M. Wuts, Protective groups in organic synthesis, John Wiley & Sons, Inc., 2nd. Ed., (1991), 309–405]. The compounds of formula (II), (III) and (V) are known or easily prepared according to known methods.

Also the oximes of formula (IX) are known compounds and can be prepared according to conventional methods comprising, for instance, the reaction of Erythromycin A or 6-0-methylerythromycin A with hydroxylamine hydrochloride.

The esters of formula (VI) can be optionally prepared according to an alternative synthetic method comprising, at first, the condensation of a suitable amino acid of formula (II) with an amino ester of formula (V), to obtain the compounds of formula $$HN(R_1)-(CH_2)_{m-1}-CON(R_2)-(CH_2)_{r-1}-COOR_4 \quad (X)$$

wherein $R_1$, $R_2$, $R_4$, m and r, have the above reported meanings.

It is clear to the man skilled in the art that before carrying out the condensation between the amino acid of formula (II) and the amino ester of formula (V) it can be necessary to suitably protect according to what already reported for the sulphonylation reaction, the amino group of the amino acid of formula (II). The further condensation of the compounds of formula (X) with a compound of formula (III), carried out according to conventional techniques and the optional deprotection allow then to obtain the compounds of formula (VI).

The preparation of the compounds of formula (I) wherein at least one of the two $R_1$ and $R_2$ substituents represents a group selected among ethyl, n.propyl, n.butyl and isobutyl, can be carried out according to an alternative synthetic method which is described hereinafter. Said method comprises, at first, the acylation of the nitrogen atom or atoms of the amino alcohols of formula (VII) wherein one or both $R_1$ and $R_2$ substituents represent a hydrogen atom.

For instance, by using a compound of formula (VII) wherein both $R_1$ and $R_2$ substituents represent a hydrogen atom and by working according to conventional techniques in the presence of a suitable acyl chloride (R'COCl), it is possible to obtain the compounds of formula

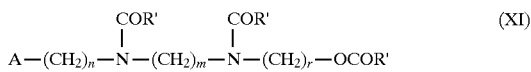

wherein

A, n, m and r have the above reported meanings;

R' represents a straight or branched $C_1$–$C_3$ alkyl group.

The reduction of the compounds of formula (XI), carried out according to conventional methods, allows to obtain the compounds of formula

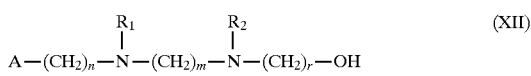

wherein

A, n, m and r have the above reported meanings;

$R_1$ and $R_2$ represent ethyl, n.propyl, n.butyl or isobutyl groups;

which, converted into the corresponding sulphonyl derivatives and condensed with the oximes of formula (IX), analogously to what previously reported, allow to obtain the compounds of formula

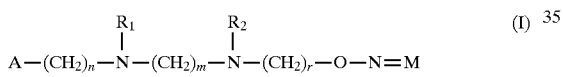

wherein

A, M, n, m and r have the above reported meanings;

$R_1$ and $R_2$ represent ethyl, n.propyl, n.butyl or isobutyl groups.

An alternative synthetic process with respect to those previously reported for the preparation of the compounds of formula (I), object of the present invention, is described hereinafter. Said process comprises, at first, the oxidation of a suitable N-protected amino alcohol such as, for instance, an N-benzyloxycarbonyl-amino alcohol of formula (XIII), in the presence of sodium hypochlorite and of the free radical 2,2,6,6-tetramethylpiperidinooxy (TEMPO), in an inert organic solvent, to obtain the compounds of formula (XIV)

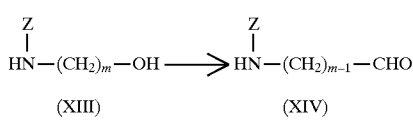

wherein m has the above reported meanings;

Z represents a protecting group.

Examples of inert organic solvents usable in the oxidation reaction are, for instance, methylene chloride, chloroform, carbon tetrachloride, 1,2-dichloroethane, ethyl acetate, benzene and toluene. The amination of the thus obtained aldehyde in the presence of a suitable amino alcohol of formula (XV) and the reduction of the formed intermediate, for instance in the presence of sodium boron hydride, allow to obtain the amino alcohols of formula (XVI)

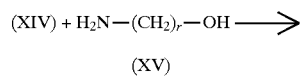

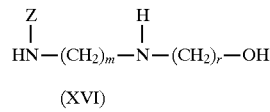

wherein

Z, m and r have the above reported meanings.

The further protection of the compounds of formula (XVI) at the amino nitrogen and, in this order, the conversion into the corresponding sulphonyl derivatives, the condensation with the oximes of formula (IX) and the deprotection at the nitrogen atoms, analogously to what previously reported, allow to obtain the compounds of formula

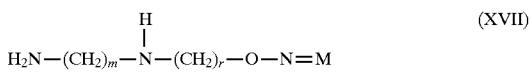

wherein

M, m and r have the above reported meanings.

The intermediate oximes of formula (XVII), condensed with a suitable aldehyde of formula (XVIII) and reduced, for instance by catalytic hydrogenation, allow to obtain the compounds of formula (I)

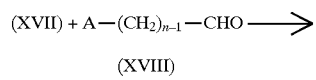

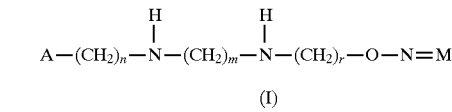

wherein

A, M, n, m and r have the above reported meanings.

The compounds of formula (XIII), (XV) and (XVIII) are known or easily prepared according to known methods.

The compounds of formula (I) wherein one or both $R_1$ and $R_2$ substituents represent a hydrogen atom, prepared according to one of the previously described methods, can be optionally alkylated at the nitrogen atom or atoms of the di-amino moiety according to conventional methods comprising, for instance, the condensation with a suitable aldehyde and the reduction of the obtained intermediate. The compounds of formula (I) wherein $R_1$ and $R_2$, the same or different, represent a straight or branched $C_1$–$C_4$ alkyl group are thus obtained.

The preparation of the compounds of formula (I) with Z or E configuration is carried out according to one of the synthetic schemes above described, by using the oxime of formula (IX) in the desired configuration [J. C. Gasc et al., The Journal of Antibiotics, 44, 313–330, (1991)].

The compounds of formula (I) are endowed with antibacterial activity against several Gram-positive and Gram-negative microorganisms and are useful in clinical and veterinary therapy for the treatment of several infectious diseases such as, for instance, the infections of the central nervous system, of the upper and lower respiratory tract, of the gastrointestinal tract, of the urogenital tract, of the odontological tissue and of the external organs such as skin, eye and ear.

Said compounds, furthermore, resulted to be active with respect to several Gram-positive microorganisms of clinical interest, resistant to Erythromycin A or, more in general, to macrolide antibiotics characterized by the presence of a 14 or 15 members macrolactone. The antibacterial activity of the compounds of formula (I) against Gram-positive microorganisms such as *Streptococcus pyogenes, Streptococcus pneumoniae, Enterococcus faecalis* and *Staphylococcus aureus* and Gram-negative microorganisms such as *Escherichia coli* and *Klebsiella pneumoniae* was evaluated by means of in vitro tests suitable to evaluate the minimum concentration of antibiotic enabling the inhibition of the bacterial growth (MIC) (example 23). Roxithromycin and Clarithromycin were used as reference compounds [The Merck Index, XI Ed., No. 8253 and 2340, respectively].

The antibacterial activity of the compounds of formula (I) against Gram-positive microorganisms resulted to be practically comparable to that of Roxithromycin and Clarithromycin, macrolides both characterized by a high antibacterial activity in vitro (table 1). With respect to Gram-negative microorganisms and, particularly, against enterobacteria such as *Escherichia coli* and *Klebsiella pneumoniae*, the compounds of formula (I) resulted to be markedly more active than both reference compounds (table 2).

To this extent, it is interesting to point out that the compounds of formula (I), object of the present invention, resulted to be more active than Roxithromycin, described in the aforementioned European patent application No. 0033255 and chosen as election compound with respect to several other derivatives such as, for instance, Erythromycin A 9-[0-[(2-dimethylamino)ethyl]oxime] [J. C. Gasc et al., The Journal of Antibiotics 44, 313–330, (1991)].

Moreover, the compounds of formula (I) resulted to be active in vivo (table 3).

The in vivo antibacterial activity of the compounds of formula (I), expressed as average protecting dose $PD_{50}$ (mg/Kg), was evaluated by means of experimental pulmonary infection induced in mouse by *Streptococcus pyogenes* (example 23).

By considering the data of activity in vivo it is evident that the compounds of formula (I) are characterized by a prolonged duration of action and a long half-life of tissue elimination.

In fact, after intraperitoneal administration in mouse, the compounds of formula (I) are rapidly and widely distributed in the whole organism and the tissue levels result to be higher than the plasmatic ones.

This results particularly evident by considering the $PD_{50}$ values for the compounds of formula (I) administered 24 hours before or 1 hour after the infection.

Said values, in fact, result to be substantially unchanged after administration 24 hours before or 1 hour after the infection. In the case of experimental pulmonary infection induced in mouse by *Streptococcus pyogenes*, a pathogen traditionally responsible for respiratory diseases, effective concentrations of the compounds of formula (I) intraperitoneally administered, persist at pulmonary level 24–48 hours after the administration.

The reference compounds Roxithromycin and Clarithromycin administered 24 hours before the infection, instead, resulted to be inactive.

Therefore, the compounds of formula (I) result also to be endowed with a pulmonary selectivity and can be advantageously used in the treatment of the infections of the respiratory tract.

In addition to the aforementioned activity against bacterial microorganisms the compounds of formula (I), object of the present invention, resulted to be active against eukaryotic pathogens. In particular, they resulted to be markedly active against protozoa such as Plasmodium falciparum which is the well-known malaria parasite.

The compounds of formula (I), therefore, can also be advantageously used in the treatment of malarian diseases.

Besides being characterized by a wide spectrum of antibiotic activity against Gram-positive and Gram-negative microorganisms and protozoa, by a good stability to the acids and by good pharmacokinetic properties, the compounds of formula (I) present, in mouse, an acute toxicity comparable to that of Roxithromycin. Therefore, being characterized by a high safety of use, they can be advantageously employed in human and veterinary therapy. The compounds of formula (I) will be preferably used in a suitable pharmaceutical form useful to oral, parenteral, suppository or topical administration.

Object of the present invention, therefore, are the pharmaceutical compositions containing a therapeutically effective amount of one or more compounds of formula (I) in admixture with a pharmaceutically acceptable carrier.

Said pharmaceutical forms comprise tablets, capsules, syrups, injectable solutions ready to use or to be prepared when used by dilution of a lyophilized, suppositories, solutions, creams, ointments and eye lotions.

For the veterinary use, in addition to the above compositions, it is possible to prepare solid or liquid concentrates to be diluted into the feed or drinking water.

According to the type of composition, besides a therapeutically effective amount of one or more compounds of formula (I), they will contain solid or liquid excipients or diluents for pharmaceutical or veterinary use and optionally other additives of normal formulating use such as thickeners, aggregants, lubricants, disgregants, flavouring and colouring agents.

In order to treat particular infections, the compound of formula (I) could be in association with an effective amount of another active ingredient.

The effective amount of the compound of formula (I) can vary according to different factors such as the seriousness and the phase of the infection, the organ or the system affected, the characteristics of the host species, the susceptibility of the bacterial species responsible for the infection and the selected route of administration.

The therapeutic dose will be generally comprised between 0.5 and 100 mg/Kg of body weight/day and could be administered into a single dose or into more daily doses.

With the aim of illustrating the present invention, without limiting it, the following examples are now given.

The structures of the compounds of formula (I) and of the synthetic intermediates for their preparation were confirmed by $^1$H-NMR or by $^{13}$C-NMR spectroscopy. The values of the meaningful signals of the more advanced intermediates and of the compounds of formula (I) are reported hereinafter.

EXAMPLE 1

Preparation of N-benzoyl-6-aminohexanoic acid

A solution of benzoyl chloride (0.18 moles) in ethyl ether (160 ml) and a solution of sodium hydroxide 1N (180 ml) were contemporaneously added to a mixture of 6-aminohexanoic acid (0.15 moles) in ethyl ether (150 ml) and water (200 ml) containing sodium hydroxide (0.15 moles), kept under stirring at a temperature comprised between 0°–5° C.

At the end of the additions, the reaction mixture was brought at room temperature and kept under stirring for other 4 hours. After separation of the phases, the aqueous phase was washed with ethyl ether (200 ml) and acidified at Congo red with concentrated hydrochloric acid.

After extraction with ethyl acetate (3×200 ml) the collected organic phases were washed with a saturated aqueous solution of sodium chloride (200 ml), dried on sodium sulphate and evaporated at reduced pressure.

N-benzoyl-6-aminohexanoic acid, used as such in the subsequent reactions, was thus obtained.

By working analogously the following compounds were prepared:
N-benzoyl-3-aminopropanoic acid;
N-benzoyl-qlycine;
N-benzoyl-8-aminooctanoic acid;
N-benzoyl-4-aminobutanoic acid;
N-phenylacetyl-6-aminohexanoic acid;
N-phenylacetyl-qlycine;
N-benzoyl-N-isopropyl-4-aminobutanoic acid;
N-benzoyl-N-isopropyl-6-aminohexanoic acid.

EXAMPLE 2

Preparation of N-[6-(benzoylamino)hexanoyl] glycine ethyl ester

A solution of dicyclohexylcarbodiimide (112 mmoles) in anhydrous tetrahydrofuran (44 ml) was gradually added to a suspension of N-benzoyl-6-aminohexanoic acid (93.5 mmoles), prepared as described in example 1, glycine ethyl ester hydrochloride (112 mmoles), triethylamine (112 mmoles) and anhydrous 1-hydroxybenzotriazole (112 mmoles) in tetrahydrofuran (330 ml), kept under stirring at 0° C. The reaction mixture was brought at room temperature and kept under stirring for 16 hours.

At the end, a precipitate was formed which was eliminated by filtration and the thus obtained filtrate was evaporated at reduced pressure. The residue was collected with ethyl acetate (300 ml) and subsequently washed with a solution of hydrochloric acid at 5% (2×100 ml), with a saturated solution of sodium chloride (100 ml), with a solution of sodium bicarbonate at 5% (2×100 ml) and, at last, with a saturated solution of sodium chloride (100 ml).

The organic phase was dried on sodium sulphate and evaporated to dryness at reduced pressure, thus obtaining N-[6-(benzoylamino)hexanoyl]glycine ethyl ester which was used as such in the subsequent reactions.

By working analogously the following compounds were prepared:
N-[(benzoylamino)acetyl]glycine ethyl ester;
N-[6-(phenylacetylamino)hexanoyl]glycine ethyl ester;
N-[(phenylacetylamino)acetyl]glycine ethyl ester;
ethyl 6-[6-(benzoylamino)hexanoylamino]hexanoate;
N-[5-(benzoylamino)pentanoyl]glycine methyl ester;
methyl 6-[5-(benzoylamino)pentanoylamino]hexanoate;
N-[7-(benzoylamino)heptanoyl]glycine methyl ester;
methyl 5-[6-(benzoylamino)hexanoylamino]pentanoate;
methyl 6-[(benzoylamino)acetylamino]hexanoate;
methyl 3-[6-(benzoylamino)hexanoylamino]propionate;
ethyl 6-[N-isopropyl-(phenylacetylamino)acetylamino] hexanoate;
methyl 6-[4-(benzoylamino)butanoylamino]hexanoate;
methyl 4-[N-isopropyl-4-(N'-isopropyl-N'-benzoylamino) butanoylamino]butanoate.

EXAMPLE 3

Preparation of N-(6-aminohexanoyl)qlycine ethyl ester a) 6-Aminohexanoic acid (100 g; 0.762 moles) and, gradually, a solution of di-tert-butyl dicarbonate (168 g; 0.762 moles) in methanol (140 ml) were added to a solution of sodium hydroxide (33.54 g; 0.831 moles) in water (840 ml) and methanol (400 ml). The reaction mixture was kept under stirring at room temperature for 4 hours.

After that, solid di-tert-butyl dicarbonate (17.5 g; 0.08 moles) was added again, keeping under stirring for other 16 hours. The reaction mixture was then washed with hexane (2×400 ml), acidified up to pH 1.5 with a solution of potassium bisulphate and extracted with ethyl acetate (3×450 ml).

The collected organic phases were dried on sodium sulphate and evaporated to dryness affording thus 6-(tert-butoxycarbonylamino)hexanoic acid as an oil (163 g).

b) By working analogously to what described in example 2, 6-(tert-butoxycarbonylamino)hexanoic acid (163 g) was directly condensed with glycine ethyl ester hydrochloride (118 g; 0.845 moles), obtaining thus N-[6-(tert-butoxycarbonylamino)hexanoyl]glycine ethyl ester (285 g) as a raw product which was used as such in the subsequent reaction.

m.p. 76°–77° C. (isopropyl ether)

c) A solution of hydrochloric acid 6N (150 ml) in ethyl acetate (150 ml) was added to a solution of N-[6-(tert-butoxycarbonylamino)hexanoyl]glycine ethyl ester (285 g) in ethyl acetate (500 ml), kept under stirring at room temperature.

After 24 hours a precipitate was formed which was filtered, washed with ethyl acetate and with ethyl ether, and dried in oven (50° C.) under vacuum.

N-(6-aminohexanoyl)glycine ethyl ester (93 g) was thus obtained as a raw product which was used as such in the subsequent reactions. TLC (methylene chloride:methanol:ammonia=10:2:1) Rf=0.2.

EXAMPLE 4

Preparation of N-[6-[(4-fluorobenzoyl)amino] hexanoyl]glycine ethyl ester

A solution of 4-fluorobenzoyl chloride (47.4 mmoles) in methylene chloride (30 ml) was gradually added to a suspension of N-(6-aminohexanoyl)glycine ethyl ester (39.5 mmoles), prepared as described in example 3, and triethylamine (87 mmoles) in methylene chloride (150 ml), kept under stirring at 0° C.

The thus prepared mixture, to which triethylamine (2 ml) was subsequently added, was brought at room temperature and kept under stirring.

After one hour under these conditions, the reaction mixture was washed with a solution of hydrochloric acid at 5% (2×100 ml) and with a saturated solution of sodium chloride (3×100 ml).

The separated organic phase was dried on sodium sulphate and evaporated to dryness under vacuum.

N-[6-[(4-fluorobenzoyl)amino]hexanoyl]glycine ethyl ester was thus obtained as a crude product, used as such in the subsequent reactions.

m.p. 121°–122° C. (ethyl acetate); TLC (ethyl acetate) Rf=0.3

By working analogously the following compound was prepared:
N-6-(2-furoylamino)hexanoyl]glycine ethyl ester
m.p. 104°–106° C. (acetonitrile/isopropyl ether); TLC (methylene chloride:methanol=95:5) Rf=0.3.

EXAMPLE 5

Preparation of N-[6-[(4-methoxybenzoyl)amino] hexanoyl]qlycine ethyl ester

By working analogously to what described in example 2 and by using 4-methoxybenzoic acid (33 mmoles) and N-(6-aminohexanoyl)glycine ethyl ester (39.5 mmoles), prepared as described in example 3, N-[6-[(4-methoxybenzoyl)amino]hexanoyl]glycine ethyl ester was obtained as a crude product, used as such in the subsequent reactions.

m.p. 106°–107° C.; TLC (methylene chloride:methanol=90:10) Rf=0.46

By working analogously the following compounds were prepared:

N-[6-[(3,4-methylenendioxybenzoyl)amino]hexanoyl] glycine ethyl ester

TLC (methylene chloride:methanol=90:10) Rf=0.39;

N-[6-[(4-methylsulphonylbenzoyl)amino]hexanoyl]glycine ethyl ester m.p. 124°–126° C.; TLC (methylene chloride:methanol=96:4) Rf=0.31;

N-[6-[(3-trifluoromethylbenzoyl)amino]hexanoyl]glycine ethyl ester m.p. 102°–104° C.; TLC (methylene chloride:methanol=95:5) Rf=0.38.

EXAMPLE 6

Preparation of 2-[6-(phenylmethylamino)hexylamino]ethanol

Sulphuric acid 6N in ethyl ether (40.9 ml; 700 mmoles), prepared by mixing sulphuric acid 96% (33 ml) and ethyl ether (100 ml), was gradually added to a suspension of N-[6-(benzoylamino)hexanoyl]glycine ethyl ester (46.8 mmoles), prepared as described in example 2, and sodium boron hydride (700 mmoles) in anhydrous tetrahydrofuran (200 ml), kept under stirring at a temperature comprised between 15° C. and 20° C.

The reaction mixture was brought at boiling temperature for 24 hours and, subsequently, cooled at 0° C.

Methanol (150 ml) was then added under stirring.

The solvent was evaporated at reduced pressure and the residue was collected with a solution of sodium hydroxide 6N (200 ml), keeping the resultant mixture at the boiling temperature for 24 hours. The reaction mixture, cooled at room temperature, was then extracted with tetrahydrofuran (2×100 ml) and the organic phase was evaporated to dryness, collected with ethyl acetate and dried on sodium sulphate.

Through acidification with an etheral solution of hydrochloric acid a precipitate constituted by 2-[6-(phenylmethylamino)hexylamino]ethanol as hydrochloride salt was obtained.

The thus obtained product was used as such in the subsequent reactions.

By working analogously the following compounds were prepared:

2-[2-(phenylmethylamino)ethylamino]ethanol;
2-[6-(2-phenylethylamino)hexylamino]ethanol;
6-[6-(phenylmethylamino)hexylamino]hexanol;
2-[5-(phenylmethylamino)pentylamino]ethanol;
2-[8-(phenylmethylamino)octylamino]ethanol;
5-[6-(phenylmethylamino)hexylamino]pentanol;
6-[3-(phenylmethylamino)propylamino]hexanol;
3-[6-(phenylmethylamino)hexylamino]propanol;
3-[4-(phenylmethylamino)butylamino]propanol;
6-[2-(phenylmethylamino)ethylamino]hexanol;
6-[N-isopropyl-4-(phenylmethylamino)butylamino]hexanol;
2-[6-[(4-fluorophenyl)methylamino]hexylamino]ethanol;
2-[6-[(4-methoxyphenyl)methylamino]hexylamino]ethanol;
2-[6-[(3,4-methylenedioxyphenyl)methylamino]hexylamino]ethanol;
2-[6-[(3-trifluoromethylphenyl)methylamino]hexylamino]ethanol;
2-[6-[(4-methylsulphonylphenyl)methylamino]hexylamino]ethanol;
4-[N-isopropyl-4-(N'-isopropyl-N'-phenylmethylamino)butylamino]butanol.

EXAMPLE 7

Preparation of 6-[N-acetyl-6-(N'-acetyl-N'-phenylmethylamino)hexylamino]hexyl acetate Triethylamine (1.95 ml; 14 mmoles) and a solution of acetyl chloride (0.62 ml; 8.69 mmoles) in methylene chloride (5 ml) were gradually added to a suspension of 6-[6-(phenylmethylamino)hexylamino]hexanol (1 g; 2.6 mmoles), prepared as described in example 6, in methylene chloride (15 ml), kept under stirring at 0° C.

After one hour under stirring at 0° C., the reaction mixture was brought at room temperature and kept under stirring for other 16 hours.

The reaction mixture was then washed with a solution of hydrochloric acid at 10% (10 ml) and with a saturated solution of sodium chloride.

After separation of the phases, the organic phase was dried on sodium sulphate and evaporated to dryness under vacuum, obtaining thus 6-[N-acetyl-6-(N'-acetyl-N'-phenylmethylamino)hexylamino]hexyl acetate (1.18 g) as an oil, used as such in the subsequent reactions.

By working analogously the following compound was prepared:

2-[N-acetyl-6-[N'-acetyl-N'-(2-phenylethyl)amino]hexylamino]ethyl acetate.

EXAMPLE 8

Preparation of 6-[N-ethyl-6-(N'-ethyl-N'-phenylmethylamino)hexylamino]hexanol

By working analogously to what described in example 6 and by using 6-[N-acetyl-6-(N'-acetyl-N'-phenylmethylamino)hexylamino]hexyl acetate, prepared as described in example 7, 6-[N-ethyl-6-(N'-ethyl-N'-phenylmethylamino)hexylamino]hexanol was prepared.

By working anlogously the following compound was prepared:

2-[N-ethyl-6-[N'-ethyl-N'-(2-phenylethyl)amino]hexylamino]ethanol.

EXAMPLE 9

Preparation of 2-[N-benzyloxycarbonyl-6-(N'-benzyloxycarbonyl-N'-phenylmethylamino)hexylamino]ethanol A solution of sodium hydroxide 1N (44.5 ml) and a solution in toluene at 50% of benzyl chloroformate (44.5 mmoles) in ethyl acetate (33 ml) were gradually and contemporaneously added to a solution of 2-[6-(phenylmethylamino)hexylamino]ethanol dihydrochloride (18.5 mmoles), prepared as described in example 6, in a solution of sodium hydroxide 1N (37.1 ml) and ethyl acetate (40 ml), kept under stirring at a temperature of 0° C.

At the end of the additions, the reaction mixture was brought at room temperature and kept under stirring for 24 hours. After separation of the phases, the aqueous phase was washed with ethyl acetate (2×50 ml).

The collected organic phases were washed with a saturated solution of sodium chloride (50 ml), dried on sodium sulphate and evaporated to dryness under vacuum.

2-[N-benzyloxycarbonyl-6-(N'-benzyloxycarbonyl-N'-phenylmethylamino)hexylamino]ethanol was thus obtained as an oil, used as such in the subsequent reactions. TLC (ethyl acetate:hexane=50:50) Rf=0.20. By working analogously the following compounds were prepared:

2-[N-benzyloxycarbonyl-2-(N'-benzyloxycarbonyl-N'-phenylmethylamino)ethylamino]ethanol TLC (ethyl acetate:hexane=60:40) Rf=0.25;

6-[N-benzyloxycarbonyl-6-(N'-benzyloxycarbonyl-N'-phenylmethylamino)hexylamino]hexanol TLC (ethyl aceate:hexane=50:50) Rf=0.27;

6-[N-benzyloxycarbonyl-5-(N'-benzyloxycarbonyl-N'-phenylmethylamino)pentylamino]hexanol;

2-[N-benzyloxycarbonyl-5-(N'-benzyloxycarbonyl-N'-phenylmethylamino)pentylamino]ethanol;

2-[N-benzyloxycarbonyl-8-(N'-benzyloxycarbonyl-N'-phenylmethylamino)octylamino]ethanol;

5-[N-benzyloxycarbonyl-6-(N'-benzyloxycarbonyl-N'-phenylmethylamino)hexylamino]pentanol;

6-[N-benzyloxycarbonyl-3-(N'-benzyloxycarbonyl-N'-phenylmethylamino)propylamino]hexanol;

3-[N-benzyloxycarbonyl-6-(N'-benzyloxycarbonyl-N'-phenylmethylamino)hexylamino]propanol;

3-[N-benzyloxycarbonyl-4-(N'-benzyloxycarbonyl-N'-phenylmethylamino)butylamino]propanol;

6-[N-isopropyl-2-[N'-benzyloxycarbonyl-N'-(2-phenylethyl)amino]ethylamino]hexanol TLC (methylene chloride:methanol:ammonia=95:5:0.5) Rf=0.33;

6-[N-benzyloxycarbonyl-4-(N'-isopropyl-N'-phenylmethylamino)butylamino]hexanol

TLC (methylene chloride:methanol:ammonia=95:5:0.5) Rf=0.42;

2-[N-benzyloxycarbonyl-6-[N'-benzyloxycarbonyl-N'-[(4-fluorophenyl)methyl]amino]hexylamino]ethanol TLC (ethyl acetate:hexane=60:40) Rf=0.35;

2-[N-benzyloxycarbonyl-6-[N'-benzyloxycarbonyl-N'-[(4-methoxyphenyl)methyl]amino]hexylamino]ethanol TLC (ethyl acetate:hexane=50:50) Rf=0.2;

2-[N-benzyloxycarbonyl-6[-N'-benzloxycarbonyl-N'-[(3,4-methylenedioxyphenyl)methyl]amino]hexylamino]ethanol TLC (ethyl acetate:hexane=60:40) Rf=0.26;

2-[N-benzyloxcarbonyl-6[-N'-benzyloxcarbonyl-N'-[(3-trifluoromethylphenyl)methyl]amino]hexylamino]ethanol TLC (ethyl acetate:hexane=50:50) Rf=0.25;

2-[N-benzyloxycarbonyl-6-[N'-benzyloxycarbonyl-N'-[(4-methylsulphonylphenyl)methyl]amino]hexylamino]ethanol TLC (ethyl acetate:hexane=90:10) Rf=0.36.

EXAMPLE 10

Preparation of 2-[N-benzyloxycarbonyl-6-(N'-benzyloxycarbonyl-N'-phenylmethylamino)hexylamino]ethyl-methanesulphonate A solution of methanesulphonyl chloride (3.16 mmoles) in methylene chloride (5 ml) was gradually added to a solution of 2-[N-benzyloxycarbonyl-6-(N'-benzyloxycarbonyl-N'-phenylmethylamino)hexylamino]ethanol (2.6 mmoles), prepared as described in example 9, in methylene chloride (15 ml) containing triethylamine (0.44 ml; 3.16 mmoles), under stirring and at a temperature of 0° C.

The reaction mixture, brought at room temperature and kept under stirring for 5 hours, was added to a solution of hydrochloric acid at 5% (20 ml).

After separation of the phases, the organic phase was washed with hydrochloric acid at 5% (10 ml) and with a saturated solution of sodium chloride (3×10 ml).

The organic phase was then dried on sodium sulphate and evaporated to dryness affording thus 2-[N-benzyloxycarbonyl-6-(N'-benzyloxycarbonyl-N'-phenylmethylamino)hexylamino]ethyl-methanesulphonate, used as such in the reaction of the following example.

EXAMPLE 11

Erythromycin A (E)-9-[0-[2-[N-benzyloxycarbonyl-6-(N'-benzyloxycarbonyl-N'-phenylmethylamino)hexylamino]ethyl]oxime]

Erythromycin A (E)-9-0-oxime (627 mg; 0.84 mmoles), 18-crown-6 ether (220 mg; 0.84 mmoles) and a solution of 2-[N-benzyloxycarbonyl-6-(N'-benzyloxycarbonyl-N'-phenylmethylamino)hexylamino]ethyl-methanesulphonate (0.84 mmoles), prepared as described in example 10, in anhydrous tetrahydrofuran (5 ml) were respectively added to a suspension of potassium tert-butylate (103 mg; 0.92 mmoles) in anhydrous tetrahydrofuran (5 ml), kept at room temperature under stirring and nitrogen atmosphere.

The reaction mixture was kept under stirring at room temperature for 20 hours and, subsequently, evaporated at reduced pressure. The residue was collected with ethyl acetate (10 ml) and the thus obtained mixture was washed with a saturated solution of sodium chloride (10 ml).

The aqueous phase was extracted with ethyl acetate (2×10 ml) and the collected organic phases were dried on sodium sulphate and evaporated to dryness.

Erythromycin A (E)-9-[0-[2-[N-benzyloxycarbonyl-6-(N'-benzyloxycarbonyl-N'-phenylmethylamino)hexylamino]ethyl]oxime] was thus obtained and used as such in the subsequent reactions.

TLC (methylene chloride:methanol:ammonia=90:9:1) Rf=0.58; Mass (C.I.) (M+H)$^+$=1250; $^1$H-NMR (200 MHz, CDCl$_3$): δ (ppm): 7.38–7.10 (m, 15H, aromatics); 5.18–5.10 (m, 4H, 2 CH$_2$Ph); 3.30 (s, 3H, OCH$_3$); 2.26 (s, 6H, 2 NCH$_3$); 0.81 (t, 3H, CH$_3$CH$_2$).

By working analogously the following compounds were prepared:

Erythromycin A (E)-9-[0-[2-[N-benzyloxycarbonyl-2-(N'-benzyloxycarbonyl-N'-phenylmethylamino)ethylamino]ethyl]oxime]

TLC (methylene chloride:methanol:ammonia:90:10:1) Rf=0.5; $^1$H-NMR (200 MHz, CDCl$_3$): δ (ppm): 7.11–6.97 (m, 15H, aromatics); 5.18–4.97 (m, 4H, 2 CH$_2$Ph); 3.30 (s, 3H, OCH$_3$); 2.25 (s, 6H, 2 NCH$_3$); 0.82 (t, 3H, CH$_3$CH$_2$);

Erythromycin A (E)-9-[0-[6-[N-benzyloxycarbonyl- 6-(N'-benzyloxycarbonyl-N'-phenylmethylamino)hexylamino]hexyl]oxime]

TLC (methylene chloride:methanol:ammonia:90:10:1) Rf=0.6; $^1$H-NMR (200 MHz, CDCl$_3$): δ (ppm): 7.27–6.96 (m, 15H, aromatics); 5.05–4.92 (m, 4H, 2 CH$_2$Ph); 3.17 (s, 3H, OCH$_3$); 2.13 (s, 6H, 2 NCH$_3$); 0.70 (t, 3H, CH$_3$CH$_2$);

Erythromycin A (E)-9-[0-[6-[N-benzyloxycarbonyl-3-(N'-benzyloxcarbonyl-N'-phenylmethylamino)propylamino] hexyl]oxime]
  TLC (methylene chloride:methanol:ammonia:90:10:1) Rf=0.65; Mass (C.I.) (M+H)⁺=1194; ¹H-NMR (200 MHz, CDCl₃): δ (ppm): 7.39–7.01 (m, 15H, aromatics); 5.17–5.02 (m, 4H, 2 CH₂Ph); 3.30 (s, 3H, OCH₃); 2.27 (s, 6H, 2 NCH₃); 0.82 (t, 3H, CH₃CH₂);

Erythromycin A (E)-9-[0-[6-(N-benzyloxycarbonyl-5-(N'-benzyloxycarbonyl-N'-phenylmethylamino)pentylamino] hexyl]oxime];

Erythromycin A (E)-9-[0-[2-[N-benzyloxycarbonyl-8-(N'-benzyloxycarbonyl-N'-phenylmethylamino)octylamino] ethyl]oxime];

Erythromycin A (E)-9-[0-[2-[N-benzyloxycarbonyl-5-(N'-benzyloxycarbonyl-N'-phenylmethylamino)pentylamino] ethyl]oxime];

Erythromycin A (E)-9-[0-[5-[N-benzyloxycarbonyl-6-(N'-benzyloxycarbonyl-N'-phenylmethylamino)hexylamino] pentyl]oxime];

Erythromycin A (E)-9-[0-[3-[N-benzyloxycarbonyl-6-(N'-benzyloxycarbonyl-N'-phenylmethylamino)hexylamino] propyl]oxime];

Erythromycin A (E)-9-[0-[3-[N-benzyloxycarbonyl-4-(N'-benzyloxycarbonyl-N'-phenylmethylamino)butylamino] propyl]oxime];

Erythromycin A (E)-9-[0-[6-[N-benzyloxycarbonyl-2-[N'-benzyloxycarbonyl-N'-(2-phenylethyl)amino] ethylamino]hexyl]oxime]
  m.p. 74°–76° C. Mass (C.I.) (M+H)⁺=1172; ¹H-NMR (200 MHz, CDCl₃): δ (ppm): 7.38–7.03 (m, 10H, aromatics); 5.13–5.03 (m, 2H, CH₂Ph); 3.29 (s, 3H, OCH₃); 2.25 (s, 6H, 2 NCH₃);

Erythromycin A (E)-9-[0-[6-[N-ethyl-6-(N'-ethyl-N'-phenylmethylamino)hexylamino]hexyl])oxime] (Compound 1)
  m.p. 80°–82° C. (acetonitrile); Mass (C.I.) (M+H)⁺=1094; ¹³C-NMR (50 MHz, CDCl₃): δ (ppm): 175.20; 171.35; 140.06; 128.86; 128.07; 126.62; 102.96; 96.27; 53.54;

Erythromycin A (E)-9-[0-[2-[N-ethyl-6-[N'-ethyl-N'-(2-phenylethyl)amino]hexylamino]hexyl])oxime] (Compound 2)
  TLC (chloroform:hexane:triethylamine=45:45:10) Rf=0.2 Mass (C.I.) (M+H)⁺=1052; ¹H-NMR (200 MHz, CDCl₃): δ (ppm): 7.26–7.04 (m, 5H, aromatics); 3.22 (s, 3H, OCH₃); 2.20 (s, 6H, 2 NCH₃); 0.79 (t, 3H, CH₃CH₂);

Erythromycin A (E)-9-[0-[6-[N-benzyloxycarbonyl-4-(N'-isopropyl-N'-phenylmethylamino)butylamino]hexyl] oxime]
  m.p. 75°–77° C.; ¹H-NMR (200 MHz, CDCl₃): δ (ppm): 7.47–7.12 (m, 10H, aromatics); 5.18–4.97 (m, 4H, 2 CH₂Ph); 3.30 (s, 3H, OCH₃); 2.25 (s, 6H, 2 NCH₃); 0.82 (t, 3H, CH₃CH₂);

Erythromycin A (E)-9-[0-[2-[N-benzyloxycarbonyl-6-[N'-benzyloxycarbonyl-N'-[(4-fluorophenyl)methyl]amino] hexylamino]ethyl]oxime]
  TLC (methylene chloride:methanol:ammonia=90:10:1) Rf=0.62; ¹H-NMR (200 MHz, CDCl₃): δ (ppm): 7.38–6.88 (m, 15H, aromatics); 5.17–5.03 (m, 2H, CH₂Ph); 3.29 (s, 3H, OCH₃); 2.26 (s, 6H, 2 NCH₃); 0.81 (t, 3H, CH₃CH₂);

Erythromycin A (E)-9-[0-[2-[N-benzyloxycarbonyl-6-[N'-benzyloxycarbonyl-N'-[(4-methoxyphenyl)methyl] amino]hexylamino]ethyl]oxime]
  TLC (methylene chloride:methanol:ammonia=45:45:10) Rf=0.3; ¹H-NMR (200 MHz, CDCl₃): δ (ppm): 7.40–7.23 (m, 10H, 2 PhCH₂O); 7.20–6.75 (m, 4H, PhOCH₃); 5.52–5.17 (m, 4H, 2 CH₂Ph); 3.77 (s, 3H, PhOCH₃); 3.29 (s, 3H, OCH₃); 2.25 (s, 6H, 2 NCH₃); 0.82 (t, 3H, CH₃CH₂);

Erythromycin A (E)-9-[0-[2-[N-benzyloxycarbonyl-6-[N'-benzyloxycarbonyl-N'-[(3,4-methylenedioxyphenyl) methyl]amino]hexylamino]ethyl]oxime]
  TLC (methylene chloride:methanol:ammonia=95:5:0.5) Rf=0.31; ¹H-NMR (200 MHz, CDCl₃): δ (ppm): 7.38–7.22 (m, 10H, 2 PhCH₂O); 6.78–6.55 (m, 3H, aromatics); 5.90 (s, 2H, OCH₂O); 5.15–5.02 (m, 4H, 2 CH₂Ph); 3.29 (s, 3H, OCH₃); 2.26 (s, 6H, 2 NCH₃); 0.82 (t, 3H, CH₃CH₂);

Erythromycin A (E)-9-[0-[2-[N-benzyloxycarbonyl-6-[N'-benzyloxycarbonyl-N'-[(3-trifluoromethylphenyl) methyl]amino]hexylamino]ethyl]oxime]
  TLC (methylene chloride:methanol:ammonia=90:10:1) Rf=0.65; ¹H-NMR (200 MHz, CDCl₃): δ (ppm): 7.54–7.15 (m, 14H, aromatics); 5.20–5.03 (m, 4H, 2 CH₂Ph); 3.30 (s, 3H, OCH₃); 2.26 (s, 6H, 2 NCH₃); 0.82 (t, 3H, CH₃CH₂);

Erythromycin A (E)-9-[0-[2-[N-benzyloxycarbonyl-6-[N'-benzyloxycarbonyl-N'-[(4-methylsulphonylphenyl) methyl]amino]hexylamino]ethyl]oxime]
  TLC (methylene chloride:methanol:ammonia=95:5:0.5) Rf=0.5; ¹H-NMR (200 MHz, CDCl₃): δ (ppm): 7.90–7.79 (m, 4H, PhSO₂CH₃); 7.48–7.15 (m, 10H, 2 PhCH₂O); 5.19–5.03 (m, 4H, 2 CH₂Ph₂); 3.30 (s, 3H, OCH₃); 3.02 (s, 3H, CH₃SO₂); 2.27 (s, 6H, 2 NCH₃); 0.82 (t, 3H CH₃CH₂);

Erythromycin A (E)-9-[0-[4-[N-isopropyl-4-(N'-isopropyl-N'-phenylmethylamino)butylamino]butyl]oxime] (Compound 3)
  m.p. 83°–85° C. (hexane); Mass (C.I.) (M+H)⁺=1066; ¹H-NMR (200 MHz, CDCl₃): δ (ppm): 7.37–7.10 (m, 5H, aromatics); 3.50 (s, 2H, CH₂Ph); 3.30 (s, 3H, OCH₃); 2.26 (s, 6H, 2 NCH₃); 0.82 (t, 3H, CH₃CH₂).

EXAMPLE 12

Preparation of Erythromycin A (E)-9-[0-[2-[6-(phenylmethylamino)hexylamino]ethyl]oxime] (Compound 4)

Palladium on charcoal at 10% (750 mg) was added to a solution of Erythromycin A (E)-9-[0-[2-[N-benzyloxycarbonyl-6-(N'-benzyloxycarbonyl-N'-phenylmethylamino)hexylamino]ethyl]oxime] (5.9 mmoles), prepared as described in example 11, in ethanol (150 ml). The thus prepared mixture was placed into a Parr hydrogenator loaded with hydrogen (1 bar) and kept under stirring at room temperature. After 7 hours the catalyst was filtered off and the alcoholic solution was evaporated to dryness.

Erythromycin A (E)-9-[0-[2-[6-(phenylmethylamino) hexylamino]ethyl]oxime], purified by silica gel chromatography (eluent methylene chloride:methanol:ammonia= 90:10:1) was thus obtained.

Mass (C.I.) (M+H)⁺=982; ¹³C-NMR (50 MHz, CDCl₃): δ (ppm): 140.48; 128.39; 128.11; 126.88. By working analogously the following compounds were prepared:

Erythromycin A (E)-9-[0-[2-[2-(phenylmethylamino) ethylamino]ethyl]oxime] (Compound 5)
  ¹³C-NMR (50 MHz, CDCl₃): δ (ppm): 176.51; 172.36; 140.96; 129.08; 128.95; 127.67; 103.84; 96.86; 53.35;

Erythromycin A (E)-9-[0-[6-[6-(phenylmethylamino) hexylamino]hexyl]oxime] (Compound 6)

Mass (C.I.) (M+H)$^+$=1038; $^{13}$C-NMR (50 MHz, CDCl$_3$): δ (ppm): 175.24; 171.31; 140.33; 128.37; 128.13; 126.89; 102.92; 96.27; 54.01;
Erythromycin A (E)-9-[0-[6-[3-(phenylmethylamino) propylamino]hexyl]oxime] (Compound 7)
  Mass (C.I.) (M+H)$^+$=995; $^{13}$C-NMR (50 MHz, CDCl$_3$): δ (ppm): 175.15; 171.37; 140.41; 128.38; 128.09; 126.89; 102.92; 96.27; 54.04;
Erythromycin A (E)-9-[0-[6-[5-(phenylmethylamino) pentylamino]hexyl]oxime] (Compound 8)
  $^1$H-NMR (200 MHz, CDCl$_3$): δ (ppm): 7.35–7.15 (m, 5H, aromatics); 3.75 (s, 2H, CH$_2$Ph); 2.25 (s, 6H, 2 NCH$_3$); 0.81 (t, 3H, CH$_3$CH$_2$);
Erythromycin A (E)-9-[0-[2-[8-(phenylmethyiamino) octylamino]ethyl]oxime] (Compound 9)
  $^1$H-NMR (200 MHz, CDCl$_3$): δ (ppm): 7.40–7.15 (m, 5H, aromatics); 3.75 (s, 2H, CH$_2$Ph); 3.29 (s, 3H, OCH$_3$); 2.25 (s, 6H, 2 NCH$_3$); 0.82 (t, 3H, CH$_3$CH$_2$);
Erythromycin A (E)-9-[0-[2-[5-(phenylmethylamino) pentylamino]ethyl]oxime] (Compound 10);
  $^{13}$C-NMR (50 MHz, CDCl$_3$): δ (ppm): 174.96; 172.00; 140.31; 128.39; 128.14; 126.93; 103.16; 96.20; 53.98;
Erythromycin A (E)-9-[0-[5-[6-(phenylmethylamino) hexylamino]pentyl]oxime] (Compound 11);
  $^{13}$C-NMR (50 MHz, CDCl$_3$): δ (ppm): 175.24; 171.24; 140.41; 128.38; 128.13; 126.88; 102.97; 96.28; 54.06;
Erythromycin A (E)-9-[0-[3-[6-(phenylmethylamino) hexylamino]propyl]oxime] (Compound 12);
  $^{13}$C-NMR (50 MHz, CDCl$_3$): δ (ppm): 175.23; 171.46; 140.45; 128.39; 128.13; 126.88; 102.99; 96.29; 50.06;
Erythromycin A (E)-9-[0-[3-[4-(phenylmethylamino) butylamino]propyl]oxime] (Compound 13);
  $^{13}$C-NMR (50 MHz, CDCl$_3$): δ (ppm): 175.22; 171.45; 140.35; 128.39; 128.13; 126.90; 102.98; 96.26; 53.94;
Erythromycin A (E)-9-[0-[6-[N-isopropyl-2-(2-phenylethylamino)ethylamino]hexyl]oxime] (Compound 14)
  m.p. 93°–95° C.; Mass (C.I.) (M+H)$^+$=1038; $^{13}$C-NMR (50 MHz, CDCl$_3$): δ (ppm): 174.92; 170.96; 139.71; 128.42; 128.10; 125.79; 102.62; 95.94; 50.93;
Erythromycin A (E)-9-[0-[6-[4-(N-isopropylphenylmethylamino)butylamino]hexyl]oxime] (Compound 15)
  m.p. 78°–80° C.; Mass (C.I.) (M+H)$^+$=1052; $^{13}$C-NMR (50 MHz, CDCl$_3$): δ (ppm): 175.47; 171.30; 140.95; 128.61; 128.02; 126.70; 116.87; 102.94; 53.94;
Erythromycin A (E)-9-[0-[2-[6-[(4-fluorophenyl) methylamino]hexylamino]ethyl]oxime] (Compound 16)
  Mass (C.I.) (M+H)$^+$=999.5; $^{13}$C-NMR (50 MHz, CDCl$_3$): δ (ppm): 161.88; 136.06; 129.65; 115.14;
Erythromycin A (E)-9-[0-[2-[6-[(4-methoxyphenyl) methylamino]hexylamino]ethyl]oxime] (Compound 17)
  Mass (C.I.) (M+H)$^+$=1011; $^{13}$C-NMR (50 MHz, CDCl$_3$): δ (ppm): 158.57; 132.58; 129.31; 113.76;
Erythromycin A (E)-9-[0-[2-[6-[(3,4-methylenedioxyphenyl)methylamino]hexylamino]ethyl]oxime] (Compound 18)
  Mass (C.I.) (M+H)$^+$=1025; $^{13}$C-NMR (50 MHz, CDCl$_3$): δ (ppm): 147.65; 146.44; 134.39; 121.18; 108.66; 108.06;
Erythromycin A (E)-9-[0-[2-[6-[(3-trifluoromethylphenyl) methylamino]hexylamino]ethyl]oxime] (Compound 19)
  Mass (C.I.) (M+H)$^+$=1050; $^{13}$C-NMR (50 MHz, CDCl$_3$): δ (ppm): 141.57; 131.40; 130.63; 128.76; 124.22; 124.72; 123.56;

Erythromycin A (E)-9-[0-[2-[6-[(4-methylsulphonylphenyl) methylamino]hexylamino]ethyl]oxime] (Compound 20)
  Mass (C.I.) (M+H)$^+$32 1059; $^{13}$C-NMR (50 MHz, CDCl$_3$): δ (ppm): 147.23; 138.97; 128.79; 127.49.

EXAMPLE 13

Preparation of N-benzyloxycarbonyl-6-aminohexanol

Benzyl chloroformate (50% in toluene; 84.8 ml; 0.256 moles) in ethyl acetate (171 ml) and a solution of sodium hydroxide 1N (256 ml) were gradually and contemporaneously added to a mixture of 6-aminohexanol (25 g; 0.21 moles) in ethyl acetate (250 ml) and water (200 ml), kept under stirring at 0° C.

The reaction mixture (pH 9) was brought at room temperature and kept under stirring for 5 hours.

After separation of the phases, the aqueous phase was washed with ethyl acetate (200 ml).

The collected organic phases were then washed with a saturated solution of sodium chloride (150 ml), dried on sodium sulphate and evaporated to dryness.

The residue was collected with ethyl ether (300 ml) and the formed precipitate was filtered and dried under vacuum at 50° C., affording thus N-benzyloxycarbonyl-6-aminohexanol (44.5 g). m.p. 80°–82° C.

EXAMPLE 14

Preparation of N-benzyloxycarbonyl-6-aminohexanal

A solution of potassium bromide (1.89 g; 16 mmoles) in water (31 ml) was added to a solution of N-benzyloxycarbonyl-6-aminohexanol (40 g; 0.159 moles), prepared as described in example 13, in methylene chloride (600 ml) containing the free radical 2,2,6,6-tetramethylpiperidinooxy (TEMPO) (0.248 g; 1.6 mmoles).

A solution of sodium hypochlorite (215 ml), prepared by mixing a solution of sodium hypochlorite at 7% (240 ml) with sodium bicarbonate (4.22 g) and hydrochloric acid at 5% (5 ml), in order to reach pH 8.7, was gradually added to the reaction mixture, kept under stirring at a temperature of 10° C.

At the end of the addition, after separation of the phases, the organic phase was washed with methylene chloride (2×200 ml), dried on sodium sulphate and evaporated to dryness.

N-benzyloxycarbonyl-6-amino-hexanal (39.45 g) was thus obtained as an oil.

TLC (ethyl acetate:hexane=1:1) Rf=0.41.

EXAMPLE 15

Preparation of 2-[6-(benzyloxycarbonylamino) hexylamino]ethanol

A mixture constituted by N-benzyloxycarbonyl-6-aminohexanal (35 g; 0.14 moles) and 2-aminoethanol (51.3 g; 0.84 moles) in ethanol (250 ml), in the presence of molecular sieves (3 A), was kept under stirring at room temperature for two hours.

The reaction mixture was then filtered on celite and sodium boron hydride (6.33 g; 0.168 moles) was added to the resultant solution. After 4 hours under stirring at room temperature, the reaction solvent was evaporated under vacuum and the residue was collected with water (500 ml) and ethyl acetate (500 ml).

After separation of the phases, the aqueous phase was further extracted with ethyl acetate (200 ml).

The collected organic phases were washed with a saturated solution of sodium chloride (250 ml), dried on sodium sulphate and evaporated to dryness, obtaining thus 2-[6-(benzyloxycarbonylamino)hexylamino]-ethanol (38.36 g).

TLC (ethyl acetate:methanol:ammonia=10:2:1) Rf=0.4.

EXAMPLE 16

Preparation of 2-[N-benzyloxycarbonyl-6-(benzyloxycarbonylamino)hexylamino]ethanol By working analogously to what described in example 9 and by using 2-[6-(benzyloxycarbonylamino)hexylamino] ethanol (38.3 g; 0.13 moles), prepared as described in example 15, 2-[N-benzyloxycarbonyl-6-(benzyloxycarbonylamino)hexylamino]ethanol was obtained as an oil.

TLC (ethyl acetate:hexane=65:35) Rf=0.45

EXAMPLE 17

Preparation of 2-[N-benzyloxycarbonyl-6-(benzyloxycarbonylamino)hexylamino]ethyl-methanesulphonate By working analogously to what described in example 10 and by using 2-[N-benzyloxycarbonyl-6-(benzyloxycarbonylamino)hexylamino]ethanol (20 g; 47.8 mmoles), prepared as described in example 16, 2-[N-benzyloxycarbonyl-6-(benzyloxycarbonylamino) hexylamino]ethyl-methanesulphonate (24.35 g) was obtained as an oil, used as such in the subsequent reactions.

EXAMPLE 18

Preparation of Erythromycin A (E)-9-[0-[2-[N-benzyloxycarbonyl-6-(benzyloxycarbonylamino) hexylamino]ethyl]oxime]

By working analogously to what described in example 11 and by using 2-[N-benzyloxycarbonyl-6-(benzyloxycarbonylamino)hexylamino]ethyl-methanesulphonate (24.25 g; 47.8 mmoles), prepared as described in example 17, after silica gel chromatography (eluent methylene chloride:methanol:ammonia=95:5:0.5), Erythromycin A (E)-9-[0-[2-[N-benzyloxycarbonyl-6-(benzyloxycarbonylamino)hexylamino]ethyl]oxime] (36.1 g) was obtained.

TLC (methylene chloride:methanol:ammonia=85:15:1.5) Rf=0.5; $^1$H-NMR (200 MHz, CDCl$_3$): δ (ppm): 7.39–7.22 (m, 10H, aromatics); 5.14–5.05 (m, 4H, 2 CH$_2$Ph); 3.29 (s, 3H, OCH$_3$); 2.25 (s, 6H, 2 NCH$_3$); 0.80 (t, 3H, CH$_3$CH$_2$).

EXAMPLE 19

Preparation of Erythromycin A (E)-9-[0-[2-(6-amino-hexylamino)ethyl]oxime]

By working analogously to what described in example 12 and by using Erythromycin A (E)-9-[0-[2-[N-benzyloxycarbonyl-6-(benzyloxycarbonylamino) hexylamino]ethyl]oxime], prepared as described in example 18, after silica gel chromatography (eluent methylene chloride: methanol:ammonia=85:15:1.5), Erythromycin A (E)-9-[0-[2-(6-aminohexylamino)ethyl]oxime] was obtained.

TLC (methylene chloride:methanol:ammonia=85:15:1.5) Rf=0.2; $^{13}$C-NMR (50 MHz, CDCl$_3$): δ (ppm): 175.18; 171.26; 102.96; 96.28.

EXAMPLE 20

Preparation of Erythromycin A (E)-9-[0-[2-[6-[(2-trifluoromethylphenyl)methylamino]hexylamino] ethyl]oxime] (Compound 21)

2-Trifluoromethylbenzaldehyde (0.4 g) and molecular sieves (4.5 g; 3 A) were added to a solution of Erythromycin A (E)-9-[0-[2-(6-aminohexylamino)ethyl]oxime] (2 g; 2.24 mmoles), prepared as described in example 19, in ethanol (50 ml), kept under stirring at room temperature.

After 2 hours, the molecular sieves were filtered off and palladium on charcoal at 10% (0.2 g) was added to the resultant solution. The reaction mixture was placed into a Parr hydrogenator which was loaded with hydrogen (1 bar).

After one hour, ended the hydrogenation reaction, the catalyst was filtered off and the solvent was evaporated.

The residue was purified by silica gel chromatography (eluent methylene chloride:methanol:ammonia=95:5:0.5), thus obtaining Erythromycin A (E)-9-[0-[2-[6-[(2-trifluoromethylphenyl)methylamino]hexylamino]ethyl] oxime] (2 g).

Mass (C.I.) (M+H)$^+$=1050; $^{13}$C-NMR (50 MHz, CDCl$_3$): δ (ppm): 139.14; 131.88; 130.38; 127.58; 126.81; 125.82.

By working analogously the following compounds were prepared:

Erythromycin A (E)-9-[0-[2-[6-(3-pyridylmethylamino) hexylamino]-ethyl]oxime] (Compound 22)

Mass (C.I.) (M+H)$^+$=982; $^{13}$C-NMR (50 MHz, CDCl$_3$): δ (ppm): 149.66; 148.39; 135.81; 123.40;

Erythromycin A (E)-9-[0-[2-[6-[(4-trifluoromethylphenyl) methylamino]hexylamino]ethyl]oxime] (Compound 23)

Mass (C.I.) (M+H)$^+$=1050; $^{13}$C-NMR (50 MHz, CDCl$_3$): δ (ppm): 144.73; 128.23; 125.25; 124.26;

Erythromycin A (E)-9-[0-[2-[6-[(2-hydroxyphenyl) methylamino]hexylamino]ethyl]oxime] (Compound 24)

Mass (C.I.) (M+H)$^+$=997; $^{13}$C-NMR (50 MHz, CDCl$_3$): δ (ppm): 158.37; 128.60; 128.19; 122.54; 118.88; 116.32;

Erythromycin A (E)-9-[0-[2-[6-[(3-hydroxyphenyl) methylamino]hexylamino]ethyl]oxime] (Compound 25)

Mass (C.I.) (M+H)$^+$=997; $^{13}$C-NMR (50 MHz, CDCl$_3$): δ (ppm): 157.28; 140.46; 129.56; 119.70; 115.55; 114.89;

Erythromycin A (E)-9-[0-[2-[6-[(4-n.butoxyphenyl) methylamino]hexylamino]ethyl]oxime] (Compound 26)

Mass (C.I.) (M+H)$^+$=1053; $^{13}$C-NMR (50 MHz, CDCl$_3$): δ (ppm): 158.27; 131.65; 129.40; 114.40;

Erythromycin A (E)-9-[0-[2-[6-[(3-phenoxyphenyl) methylamino]hexylamino]ethyl]oxime] (Compound 27)

Mass (C.I.) (M+H)$^+$=1073; $^{13}$C-NMR (50 MHz, CDCl$_3$): δ (ppm): 157.32; 157.28; 142.69; 129.72; 129.64; 123.16; 122.91; 118.84; 118.52; 117.29;

Erythromycin A (E)-9-[0-[2-[6-[(4-hydroxyphenyl) methylamino]hexylamino]ethyl]oxime] (Compound 28)

Mass (C.I.) (M+H)$^+$=997; $^{13}$C-NMR (50 MHz, CDCl$_3$): δ (ppm): 156.49; 130.00; 128.87; 115.88;

Erythromycin A (E)-9-[0-[2-[6-[(4-phenoxyphenyl) methylamino]hexylamino]ethyl]oxime] (Compound 29)

Mass (C.I.) (M+H)$^+$=1073; $^{13}$C-NMR (50 MHz, CDCl$_3$): δ (ppm): 157.43; 156.05; 135.43; 129.69; 129.49; 123.07; 118.92; 118.72; 118.67;

Erythromycin A (E)-9-[0-[2-[6-[(biphenyl-4-yl) methylamino]hexylamino]ethyl]oxime] (Compound 30)

Mass (C.I.) (M+H)$^+$=1057; $^{13}$C-NMR (50 MHz, CDCl$_3$): δ (ppm): 140.94; 139.86; 139.40; 128.74; 128.58; 127.13; 127.03;

Erythromycin A (E)-9-[0-[2-[6-[(2-furylmethylamino) hexylamino]ethyl]oxime] (Compound 31)

Mass (C.I.) (M+H)$^+$=971; $^{13}$C-NMR (50 MHz, CDCl$_3$): δ (ppm): 153.92; 141.73; 110.08; 106.81.

EXAMPLE 21

Preparation of Erythromycin A (E)-9-[0-[2-[6-[(3,5-dichloro-2-hydroxyphenyl)methylamino] hexylamino]ethyl]oxime] (Compound 32)

Molecular sieves (6 g; 3 A) and 3,5-dichloro-2-hydroxybenzaldehyde (0.535 g; 2.8 mmoles) were added to a solution of Erythromycin A (E)-9-[0-[2-(6-amino-hexylamino)ethyl]oxime] (2.5 g; 2.8 mmoles), prepared as described in example 19, in anhydrous ethanol (100 ml). The reaction mixture was kept under stirring at room temperature and, after 2 hours, the molecular sieves were filtered off and sodium boron hydride (0.106 g; 2.89 mmoles) was added, portionwise, to the resultant solution.

After 3 hours under stirring, the solvent was evaporated at reduced pressure and the residue was purified by silica gel chromatography (eluent methylene chloride:methanol:ammonia=85:15:1.5) obtaining thus Erythromycin A (E)-9-[0-[2-[6-[(3,5-dichloro-2-hydroxyphenyl)methylamino]hexylamino]ethyl]oxime] (2.2 g).

Mass (C.I.) (M+H)$^+$=1066; $^{13}$C-NMR (50 MHz, CDCl$_3$): δ (ppm): 153.43; 128.43; 126.42; 124.41; 122.91; 121.61. By working analogously the following compounds were prepared:

Erythromycin A (E)-9-[0-[2-[6-[(2-nitrophenyl) methylamino]hexylamino]ethyl]oxime] (Compound 33)

Mass (C.I.) (M+H)$^+$=1027; $^{13}$C-NMR (50 MHz, CDCl$_3$): δ (ppm): 149.14; 135.79; 133.13; 131.26; 127.87; 124.70;

Erythromycin A (E)-9-[0-[2-[6-[(3-nitrophenyl) methylamino]hexylamino]ethyl]oxime] (Compound 34)

Mass (C.I.) (M+H)$^+$=1027; $^{13}$C-NMR (50 MHz, CDCl$_3$): δ (ppm): 148.37; 142.87; 134.17; 129.22; 122.81; 121.96;

Erythromycin A (E)-9-[0-8 2-[6-[(4-nitrophenyl) methylamino]hexylamino]ethyl]oxime] (Compound 35)

Mass (C.I.) (M+H)$^+$=1027; $^{13}$C-NMR (50 MHz, CDCl$_3$): δ (ppm): 148.41; 147.00; 128.59; 123.60;

Erythromycin A (E)-9-[0-[2-[6-[(4-hydroxy-3-nitrophenyl) methylamino]hexylamino]ethyl]oxime] (Compound 36)

Mass (C.I.) (M+H)$^+$=1043; $^{13}$C-NMR (50 MHz, CDCl$_3$): δ (ppm): 157.29; 137.40; 134.05; 128.01; 125.23; 121.70;

Erythromycin A (E)-9-[0-[2-[6-[(3-hydroxy-4-nitrophenyl) methylamino]hexylamino]ethyl]oxime] (Compound 37)

Mass (C.I.) (M+H)$^+$=1043; $^{13}$C-NMR (50 MHz, CDCl$_3$): δ (ppm): 155.50; 151.98; 132.51; 125.13; 119.67; 118.59;

EXAMPLE 22

Preparation of Erythromycin A (E)-9-[0-[2-[N-methyl-6-(N'-methyl-N'-phenylmethylamino) hexylamino]ethyl]oxime] (Compound 38)

An aqueous solution of formaldehyde at 37% (2 ml; 26.6 mmoles) and palladium on charcoal at 10% (0.82 g) were added, in this order, to a solution of Erythromycin A (E)-9-[0-[2-[6-(phenylmethylamino)hexylamino]ethyl] oxime] (2 g; 2 mmoles), prepared as described in example 12, in a mixture ethanol:water=1:1 (20 ml) kept under stirring at room temperature.

The reaction mixture was placed into a Parr hydrogenator loaded with hydrogen (1 bar).

After 2 hours, the reaction mixture was filtered to eliminate the catalyst and the resultant solution was evaporated to dryness. The obtained residue was purified by silica gel chromatography (eluent methylene chloride:methanol:ammonia=90:10:1) affording Erythromycin A (E)-9-[0-[2-[N-methyl-6-(N'-methyl-N'-phenylmethylamino)hexylamino]ethyl]oxime] (1.8 g).

Mass (C.I.) (M+H)$^+$=1009; $^{13}$C-NMR (50 MHz, CDCl$_3$): δ (ppm): 139.20; 129.04; 128.17; 126.86. By working analogously the following compound was prepared:

Erythromycin A (E)-9-[0-[2-[N-methyl-6-[N'-methyl-N'-(4-trifluoromethylphenyl)methylamino]hexylamino]ethyl] oxime] (Compound 39)

Mass (C.I.) (M+H)$^+$=1078; $^{13}$C-NMR (50 MHz, CDCl$_3$): δ (ppm): 143.65; 129.12; 129.03; 125.10; 124.29.

EXAMPLE 23

Pharmacologic activity a) In vitro antibacterial activity

The determination of the minimum inhibiting concentrations (MIC), with respect to Gram-positive and Gram-negative bacteria was carried out through the micromethod of gradual broth dilution in double series [National Committee for Clinical Laboratory Standards, 1990; Methods for dilution antimicrobial susceptibility tests for bacteria that grow aerobically; Approved standards M7-A2-NCCLS, Villanova, Pa.], by using Mueller Hinton Broth (MHB) as a culture medium.

In the case of exigent bacteria, horse serum at 5% (*Streptococcus pneumoniae* and *Streptococcus pyogenes*) was added to the medium. Roxithromycin and Clarithromycin [The Merck Index, XI Ed., No. 8253 and 2340, respectively] were used as reference macrolides. MIC, expressed as (μg/ml), were determined after incubation of the microplates at 37° C. for 18 hours, evaluating the lowest antibiotic concentration enabling the inhibition of bacterial development.

b) In vivo antibacterial activity

The therapeutical effectiveness, expressed as average protecting dose (PD$_{50}$), of the considered compounds of formula (I) was evaluated by experimental pulmonary infection induced in mouse by *Streptococcus pyogenes*C 203.

Charles River albin mice (strain CD 1), of body weight comprised between 23–35 g, stabulated in groups of 6 for cage and normo-feeded with standard diet and water ad libitum were used. A suspension of *S. pyogenes* C 203 (corresponding about to 10$^8$ UFC) in tryptose broth (0.05 ml) was intranasally administered to each mouse anesthesized with a mixture of ethyl ether and chloroform.

The compounds under examination were intraperitoneally administered as a single dose, in 0.2% Tween suspension, 24 hours before or 1 hour after the infection.

Mice mortality observation was prolonged up to 10 days from the infection.

PD$_{50}$ calculation, expressed as (mg/Kg), was carried out through the analysis of probit.

For some representative compounds of formula (I) the in vitro antibacterial activity against Gram-positive microorganisms (table 1) and Gram-negative microorganisms (table 2), and the in vivo antibacterial activity values (table 3), are reported as follows.

Table 1

In vitro antibacterial activity, expressed as minimum inhibiting concentration MIC (μg/ml), of the compounds 2, 4–12, 16–19, 21, 23–38 and of the reference compounds Roxithromycin and Clarithromycin, against Gram-positive microorganisms such as *Streptococcus pneumoniae* BS 3, *Streptococcus pneumoniae* BS 4, *Streptococcus pyogenes* A 26, *Streptococcus pyogenes* C 203, *Enterococcus faecalis* ATCC 29212 and *Staphylococcus aureus* PV 14.

TABLE 1

| | MIC ($\mu$g/ml) | | | | | |
|---|---|---|---|---|---|---|
| compound | *S. pneumioniae* BS 3 | *S. pneumoniae* BS 4 | *S. pyogenes* A 26 | *S. pyogenes* C 203 | *E. faecalis* ATCC 29212 | *S. aureus* PV 14 |
| 2 | 0.0156 | 0.0312 | 0.0156 | 0.0312 | 8 | 1 |
| 4 | 0.0156 | 0.0156 | 0.0156 | 0.0039 | 4 | 0.25 |
| 5 | 0.0156 | 0.0312 | 0.0312 | 0.0156 | 4 | 1 |
| 6 | 0.0156 | 0.0312 | 0.0312 | 0.0156 | 8 | 0.25 |
| 7 | 0.0625 | 0.0625 | 0.0312 | 0.0156 | 4 | 0.5 |
| 8 | 0.25 | 0.5 | 0.0312 | 0.0078 | 8 | 0.5 |
| 9 | 0.0078 | 0.0078 | 0.0078 | 0.0039 | 4 | 0.25 |
| 10 | 0.0156 | 0.0156 | 0.0078 | 0.0039 | 4 | 0.5 |
| 11 | 0.25 | 0.5 | 0.0625 | 0.0312 | 16 | 0.5 |
| 12 | 0.25 | 0.5 | 0.0625 | 0.0312 | 16 | 0.25 |
| 16 | 0.0156 | 0.0156 | 0.0156 | 0.0039 | 4 | 0.25 |
| 17 | 0.0312 | 0.0625 | 0.0625 | 0.0039 | 4 | 0.25 |
| 18 | 0.0156 | 0.0312 | 0.0312 | 0.0078 | 2 | 0.25 |
| 19 | 0.0156 | 0.0078 | 0.0156 | 0.0156 | 2 | 1 |
| 21 | 0.0078 | 0.0039 | 0.0078 | 0.0156 | 2 | 1 |
| 23 | 0.0156 | 0.0078 | 0.0156 | 0.0156 | 2 | 1 |
| 24 | 0.0078 | 0.0156 | 0.0156 | 0.0039 | 4 | 0.25 |
| 25 | 0.25 | 0.25 | 0.125 | 0.0312 | 8 | 0.125 |
| 26 | 0.0156 | 0.0156 | 0.0312 | 0.0078 | 1 | 0.25 |
| 27 | 0.0078 | 0.0078 | 0.0156 | 0.0078 | 1 | 0.5 |
| 28 | 0.25 | 0.25 | 0.25 | 0.125 | 16 | 0.125 |
| 29 | 0.0078 | 0.0156 | 0.0312 | 0.0039 | 1 | 0.5 |
| 30 | 0.0156 | 0.0156 | 0.0156 | 0.0078 | 1 | 0.5 |
| 31 | 0.0078 | 0.0078 | 0.0078 | 0.0039 | 4 | 0.5 |
| 32 | 0.0625 | 0.0312 | 0.0625 | 0.0156 | 2 | 0.5 |
| 33 | 0.0039 | 0.0039 | 0.0039 | 0.00097 | 2 | 0.5 |
| 34 | 0.0019 | 0.0039 | 0.0078 | 0.0039 | 1 | 0.25 |
| 35 | 0.0039 | 0.0039 | 0.0078 | 0.0019 | 0.5 | 0.25 |
| 36 | 0.0625 | 0.0625 | 0.0625 | 0.0078 | 16 | 0.5 |
| 37 | 0.0312 | 0.0312 | 0.0312 | 0.0039 | 8 | 0.5 |
| 38 | 0.0078 | 0.0039 | 0.0156 | 0.0078 | 8 | 0.5 |
| Roxithromycin | 0.0312 | 0.0625 | 0.0625 | 0.0625 | 4 | 1 |
| Clarithromycin | 0.0078 | 0.0156 | 0.0078 | 0.0078 | 1 | 0.25 |

The above reported data clearly indicate that the compounds of formula (I), object of the present invention, are endowed with an antibacterial activity substantially comparable to that of Clarithromycin and Roxithromycin, with respect to Gram-positive microorganisms.

Table 2

In vitro antibacterial activity, expressed as minimum inhibiting concentration MIC ($\mu$g/ml), of the compounds 2, 4–12, 16–19, 21, 23–38 and of the reference compounds Roxithromycin and Clarithromycin, against Gram-negative microorganisms such as *Escherichia coli* ATCC 25922 and *Klebsiella pneumoniae* ZC 2.

TABLE 2

| | MIC ($\mu$g/ml) | |
|---|---|---|
| Compound | *E. coli* ATCC 25922 | *K. pneumoniae* ZC 2 |
| 2 | 16 | 64 |
| 4 | 4 | 16 |
| 5 | 8 | 32 |
| 6 | 4 | 16 |
| 7 | 4 | 16 |

TABLE 2-continued

| | MIC ($\mu$g/ml) | |
|---|---|---|
| Compound | *E. coli* ATCC 25922 | *K. pneumoniae* ZC 2 |
| 8 | 4 | 16 |
| 9 | 4 | 16 |
| 10 | 4 | 16 |
| 11 | 8 | 16 |
| 12 | 8 | 32 |
| 16 | 2 | 8 |
| 17 | 4 | 16 |
| 18 | 2 | 16 |
| 19 | 2 | 8 |
| 21 | 4 | 16 |
| 23 | 1 | 4 |
| 24 | 4 | 8 |
| 25 | 8 | 16 |
| 26 | 1 | 2 |
| 27 | 1 | 2 |
| 28 | 16 | 32 |
| 29 | 1 | 2 |
| 30 | 1 | 2 |
| 31 | 4 | 16 |
| 32 | 4 | 16 |
| 33 | 4 | 16 |
| 34 | 1 | 8 |

27

TABLE 2-continued

| | MIC (µg/ml) | |
|---|---|---|
| Compound | E. coli ATCC 25922 | K. pneumoniae ZC 2 |
| 35 | 1 | 4 |
| 36 | 8 | 32 |
| 37 | 4 | 16 |
| 38 | 8 | 32 |
| Roxithromycin | 28 | 256 |
| Clarithromycin | 64 | 128 |

The antibacterial activity of the compounds of formula (I) against Gram-negative microorganisms such as *Escherichia coli* and *Klebsiella pneumoniae* resulted to be markedly higher than that of both reference compounds.

Table 3

In vivo antibacterial activity, expressed as average protecting dose $PD_{50}$ (mg/Kg), 24 hours before and 1 hour after the experimental pulmonary infection induced in mouse by *Streptococcus pyogenes* C 203, of the compounds 4, 10, 16–19, 21, 23, 26–27, 29–30, 33–35 and 38 and of the reference compounds Roxithromycin and Clarithromycin.

TABLE 3

| | $PD_{50}$ (mg/Kg) Pulmonary infection (*S. pyogenes* C 203) | |
|---|---|---|
| Compound | 1 hour after infection | 24 hours before infection |
| 4 | 0.9 | 4.78 |
| 10 | 2.36 | 5.8 |
| 16 | 3.6 | 10.21 |
| 17 | 1.17 | 8.16 |
| 18 | 1.32 | 2.23 |
| 19 | 1.95 | 4.84 |
| 21 | 0.82 | 5.95 |
| 23 | 1.46 | 3.A9 |
| 26 | 6.11 | 6.11 |
| 27 | 15.6 | 15.6 |
| 29 | 7.65 | 6.1 |
| 30 | 19.3 | 19.3 |
| 33 | 1.61 | 6.11 |
| 34 | 1.88 | 6.8 |
| 35 | 3.00 | 6.0 |
| 38 | 11.8 | 11.8 |
| Roxithromycin | 0.9 | >25 |
| Clarithromycin | 3.25 | >50 |

The compounds of formula (i) resulted to be active in vivo and their activity profile indicates that said compounds present a duration of action and a half-life of tissue elimination significantly higher than those of both reference compounds.

We claim:

1. A compound of formula

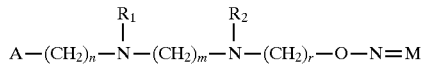

$$A-(CH_2)_n-\underset{|}{\overset{R_1}{N}}-(CH_2)_m-\underset{|}{\overset{R_2}{N}}-(CH_2)_r-O-N=M \quad (I)$$

wherein A is a phenyl group or a heterocycle with 5 or 6 members containing 1 or more heteroatoms selected from the group consisting of nitrogen, oxygen and sulphur,

28 optionally substituted with from 1 to 3 groups, the same or different, selected from the group consisting of straight or branched $C_1$–$C_4$ alkyl or alkoxy groups, $C_1$–$C_2$ alkylenedioxy groups, $C_1$–$C_4$ alkylsulphonyl groups, phenyl, phenoxy, hydroxy, carboxy, nitro, halogen and trifluoromethyl groups;

$R_1$ and $R_2$, the same or different, represent a hydrogen atom or straight or branched $C_1$–$C_4$ alkyl group;

n is 1 or 2;

m is an integer comprised between 1 and 8;

r is an integer comprised between 2 and 6;

M represents a group of the formula:

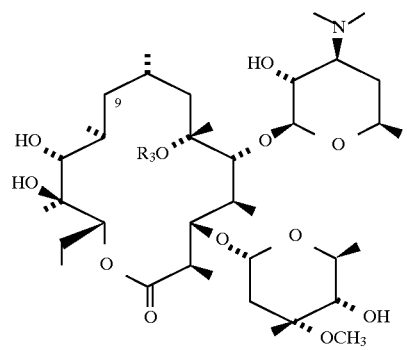

that carries the oximinyl moiety at the 9 position;

wherein $R_3$ is a hydrogen atom or a methyl group; and its pharmaceutically acceptable salts.

2. A compound according to claim 1 having E configuration.

3. A compound according to claim 1 wherein A represents a phenyl group or a heterocycle selected from the group consisting of pyridine and furan optionally substituted with from 1 to 3 groups selected from the group consisting of hydroxy, methoxy, methylenedioxy, n.butoxy, phenoxy, phenyl, methylsulphonyl, nitro, halogen and trifluoromethyl; $R_1$, and $R_2$ are the same and represent a hydrogen atom or a methyl group; $R_3$ represents a hydrogen atom.

4. A compound according to claim 1 wherein A represents a phenyl group optionally substituted with a group selected from the group consisting of phenoxy, nitro and trifluoromethyl; $R_1$, and $R_2$ are the same and represent a hydrogen atom or a methyl group; n is equal to 1, m is equal to 6; r is equal to 2; and $R_3$ represents a hydrogen atom.

5. A pharmaceutical composition containing a therapeutically effective amount of one or more compounds of claim 1 in admixture with a pharmaceutically acceptable carrier.

6. A method for the treatment of infectious diseases in human or veterinary therapy consisting in administering a therapeutically effective amount of a compound according to claim 1.

7. A method according to claim 6 for the treatment of malarian diseases.

* * * * *

UNITED STATES PATENT AND TRADEMARK OFFICE
CERTIFICATE OF CORRECTION

PATENT NO. : 5,847,092

DATED : December 8, 1998

INVENTOR(S) : Pellacini et al.

It is certified that error appears in the above-identified patent and that said Letters Patent is hereby corrected as shown below:

```
Column 28, line 8,
    Claim 1, line 5 above the structure after "or" insert --a--.
```

Signed and Sealed this

Fifteenth Day of June, 1999

*Attest:*

Q. TODD DICKINSON

*Attesting Officer*   *Acting Commissioner of Patents and Trademarks*